(12) United States Patent
Brown et al.

(10) Patent No.: US 6,184,980 B1
(45) Date of Patent: Feb. 6, 2001

(54) FIBER OPTIC SENSOR FOR PETROLEUM

(75) Inventors: Christopher W. Brown, Saunderstown, RI (US); James J. Alberts, Sapelo Island, GA (US)

(73) Assignee: The Board of Governors for Higher Education, State of Rhode Island and Providence Plantations, Providence, RI (US)

( * ) Notice: Under 35 U.S.C. 154(b), the term of this patent shall be extended for 0 days.

(21) Appl. No.: 08/394,596

(22) Filed: Feb. 27, 1995

(51) Int. Cl.[7] .................................................. G01J 3/00
(52) U.S. Cl. ........................ 356/300; 356/70; 356/440; 385/123
(58) Field of Search .............................. 356/300, 70, 440, 356/437, 301; 385/12, 13, 123, 142, 144, 126; 250/227.25, 227.16

(56) References Cited

U.S. PATENT DOCUMENTS

| | | | |
|---|---|---|---|
| 4,352,983 | * 10/1982 | Silvus, Jr. et al. | ...................... 356/70 |
| 4,620,284 | * 10/1986 | Schnell et al. | ................... 356/301 X |
| 4,955,689 | * 9/1990 | Fuller et al. | ......................... 385/123 |

FOREIGN PATENT DOCUMENTS

| 107149 | * 8/1981 | (JP) | ...................................... 356/440 |

\* cited by examiner

Primary Examiner—Donald Hajec
Assistant Examiner—Daniel St. Cyr
(74) Attorney, Agent, or Firm—Samuels, Gauthier & Stevens (57) ABSTRACT

A silver halide fiber optic for the detection and identification of petroleum. The fiber optic serves both as a waveguide for transmitting a signal to and from petroleum in remote locations and also as an intrinsic part of the sensing element to obtain evanescent wave spectra. The evanescent wave is attenuated at various wavelengths based on the chemical composition of the petroleum in which the sensor is immersed. The spectrum obtained from an unknown sample is compared with the spectrum of known samples from a library to identify the unknown sample.

5 Claims, 8 Drawing Sheets

FIBER OPTIC SENSOR FOR PETROLEUM

BACKGROUND AND BRIEF SUMMARY OF THE INVENTION

It is important to find suitable analytical techniques to detect and characterize petroleum products. Several methods have been proposed to provide identification of crude oil, fuel oil and residual distillates, Adlard, E. R., *J. Inst. Petroleum,* 1972, 58, 63; Baier, R. E., *J. Geophys. Res.,* 1972, 77, 5062; Cole, R. D., *J. Inst. Petroleum,* 1968, 54, 288; Kawahara, F. K., *J. Environ. Sci. Technol.,* 1969, 3, 150; and Mattson, J. S., *Anal. Chem.,* 1971, 43, 1872. Infrared spectroscopic data analysis has been used to identify the type and source of a large number of petroleum samples, Lynch, P. F. and Brown, C. W., *Environ. Sci. Technol.,* 1973, 13, 1123; Brown, C. W., Lynch, P. F. and Ahmadjian, M., *Anal. Chem.,* 1974, 46, 183; Brown, C. W., Lynch, P. F. and Ahmadjian, M., *Appl. Spectro. Rev.,* 1975, 9, 223; and Brown, C. W. and Lynch, P. F., *Anal. Chem.,* 1975, 48, 191. Most of these methods used bands in the region of 650–1200 cm$^{-1}$ to characterize petroleum samples, since crude oils and their various distillates provide unique finger prints in this region, which can be used to identify the source of oil slicks.

The present invention embodies a metal halide fiber optic to measure the spectra of petroleum. The fiber optic serves both as a waveguide for transmitting the signal to and from petroleum in remote locations, and also as an intrinsic part of the sensor element to obtain evanescent wave spectra. Light travels down the core of the fiber with total reflection at each interface of the core and the cladding or surrounding material of lower refractive index. Preferably, the light penetrates the cladding or surrounding material by approximately 0.1λ (λ=wavelength) and sets up a standing evanescent wave in the surrounding material. During this short penetration, the evanescent wave is attenuated at various wavelengths due to vibrational transitions of the chemical groups in the cladding or the surrounding material. Thus, the light is not totally reflected at all wavelengths because of the attenuations. The resulting absorption spectrum is referred to as evanescent wave or attenuated total reflection (ATR) spectrum of the cladding or the surrounding material.

In the preferred embodiment of the invention, a silver halide fiber without a cladding, is placed directly in a petroleum sample to obtain an evanescent spectrum of the petroleum sample.

DESCRIPTION OF THE PREFERRED EMBODIMENT(S)

Mid infrared spectra of thirty petroleum samples including crude oils, their residuals and distillates from different sources were measured in the region of 1350–700 cm$^{-1}$. The main differences in the spectra of these samples was in the intensities of the bands due to skeletal vibrations of the aromatic components and CH wagging and rocking motions. Spectra were also measured from petroleum spills on water. The spectra of petroleum spills were used as an unknown set in a library search. Principal component analysis (PCA) was used to classify the known samples by using score plots for specific loading vectors. Since the evanescent wave spectra can be easily measured by using the fiber optic sensor, this method is very useful for remote detection of petroleum in industrial and environmental analysis.

Experimental Section
Spectroscopic Measurements

Figure 1:
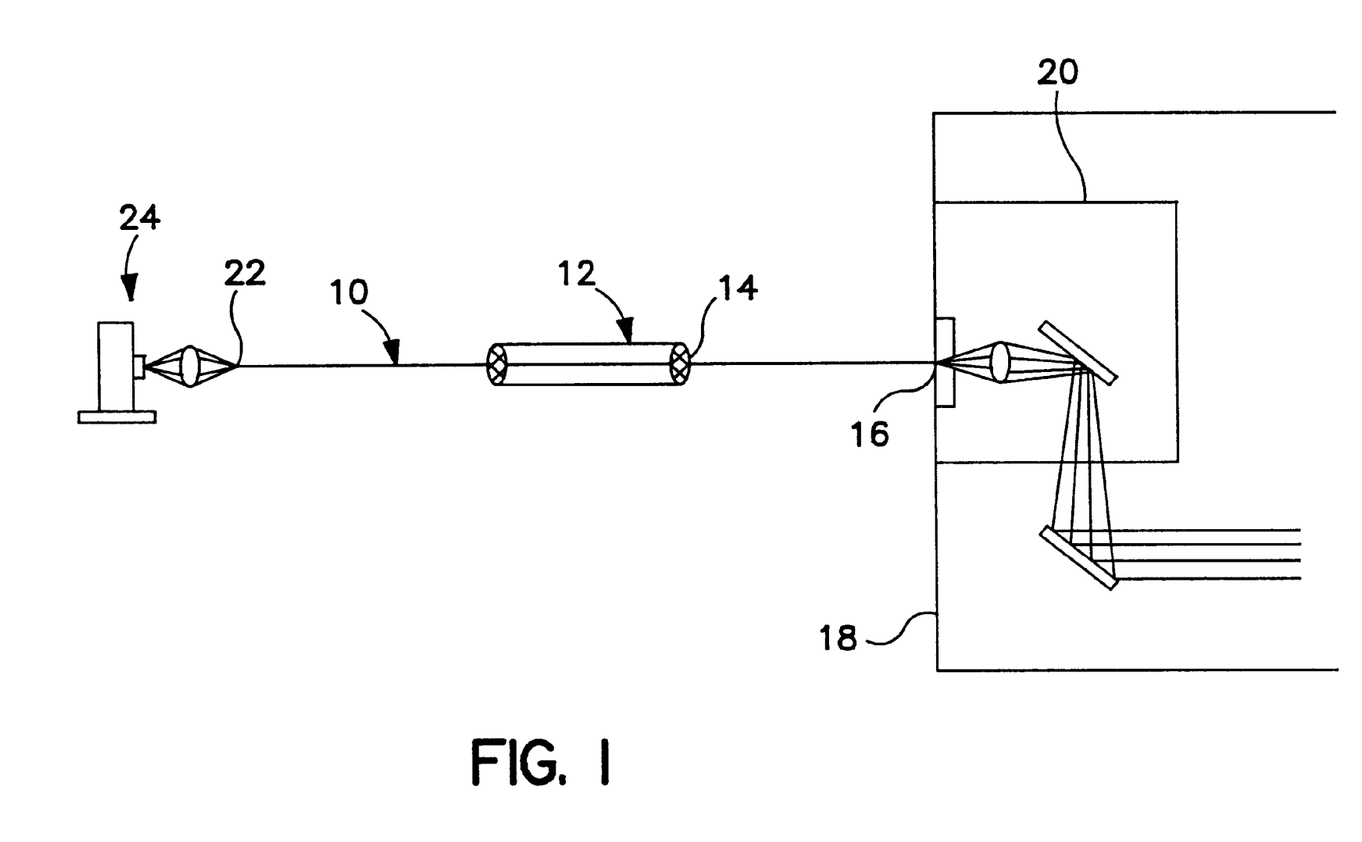
FIG. 1 is a schematic illustration of a petroleum detection system embodying the invention.

Referring to FIG. 1, a fiber optic sensor 10 was made from a 0.5 m length of silver halide fiber optic (CeramOptec, Inc., Enfield, Conn.) having a 700-μm-diameter core. The fiber is made from a mixture of silver chloride and silver bromide. The refractive index of the silver halide is 2.2. About 10 cm of the fiber without a cladding was placed in a trough 12 containing a petroleum sample 14. It is important to note that the petroleum samples adhere to the fiber and in a sense function as a cladding. The proximal end 16 of the fiber optic 10 was connected to a FTS-40 (BIO-RAD, Digilab Division, Cambridge, Mass.) spectrometer 18 through a BIO-RAD fiber optic interface accessory 20, which consists of a three-dimensional translational stage for positioning the fiber 10. The distal end 22 of the fiber optic was directed to a liquid nitrogen cooled MCT detector 24 (EG&G JUDSON; Model J15D14-M204-SO1M-60), which was placed 0.5 m from the spectrometer 18. Light in a range of 5 to 15 microns from the spectrometer was launched into the fiber optic which transmits it to the sample and then to the detector.

Evanescent wave spectra of thirty petroleum samples including fourteen crude oils, five kerosenes, four No. 2 fuels and seven residual distillates from different sources were measured. The evanescent wave spectra of these samples were measured using 128 scans at 4 cm$^{-1}$ resolution. Eight samples including five crude oils, one kerosene, one No. 2 fuel and one residual distillate randomly selected from the thirty petroleum samples were spilt onto water and used as unknown petroleum samples. Evanescent wave spectra of these unknown petroleum spills were measured under the same conditions as the original petroleum samples.

Spectral Processing

All spectra were imported into LAB CALC software (Galactic Industries Co., Salem, N.H.) for preliminary processing and display. Computer programs for performing the library search (Mix-Match, Lo, S. and Brown, C. W., *Appl. Spectro.,* 1991, 45, 1621; and Lo, S. and Brown, C. W., *Appl. Spectro.,* 1991, 45, 1628), and classification (PCA, Principal component analysis) were written in Quick Basic, and used the methods of successive average orthogonalization (SAO) developed by Donahue and Brown, Donahue, S. M. and Brown, C. W., *Anal. Chem.,* 1991, 63, 980.

Results and Discussion
Fiber Optic Spectra

Figure 2:
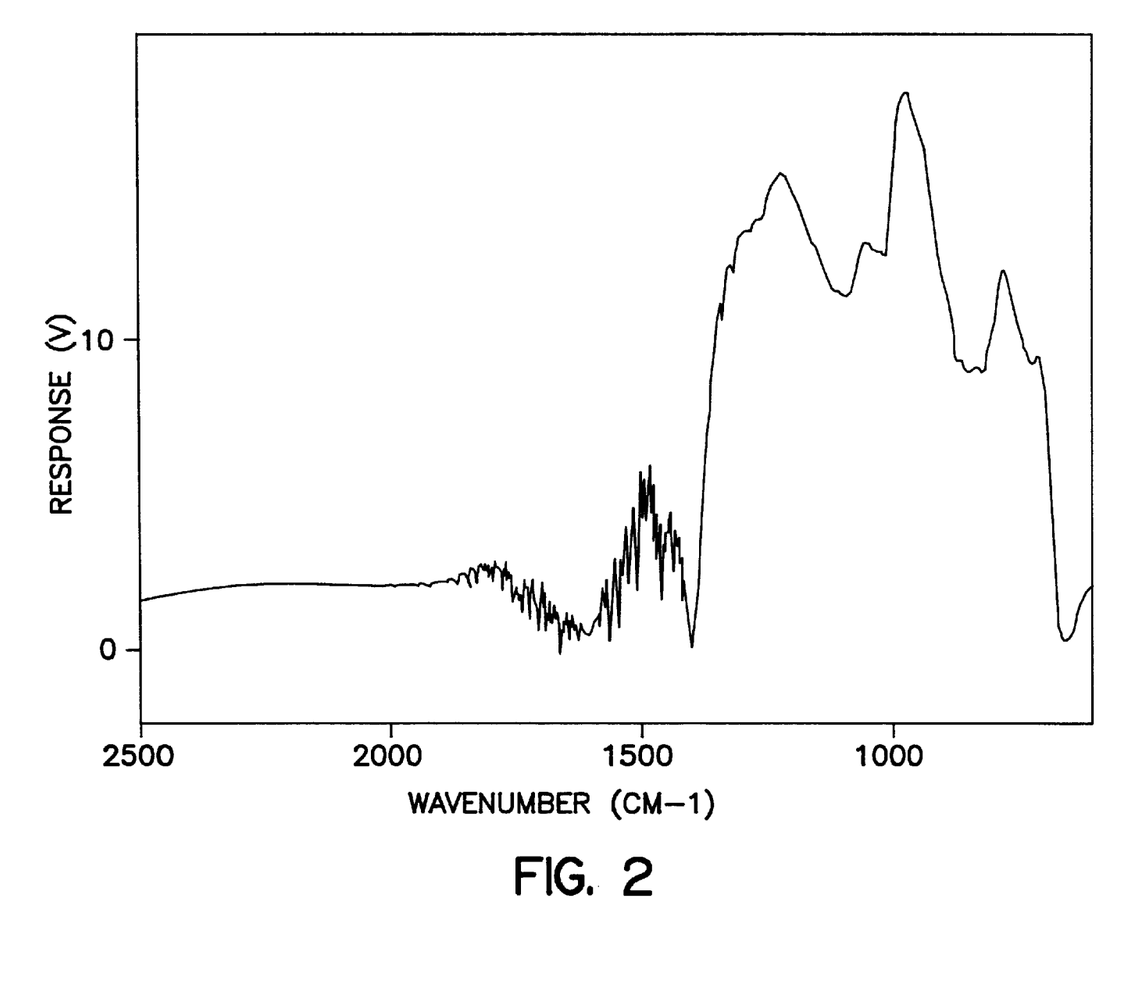
FIG. 2 is a graph of a single beam, mid-infrared spectrum of a silver halide fiber.

Referring to FIG. 2, a reference single beam spectrum of the silver halide fiber is shown. This spectrum was used as a background reference for the spectra of petroleum samples. The single beam spectrum of the fiber displays good response for the region of 1400–600 cm$^{-1}$. The attenuation loss of the fiber is about 0.2–0.4 db per meter.

Evanescent Wave Spectra of Petroleum

Figure 3:
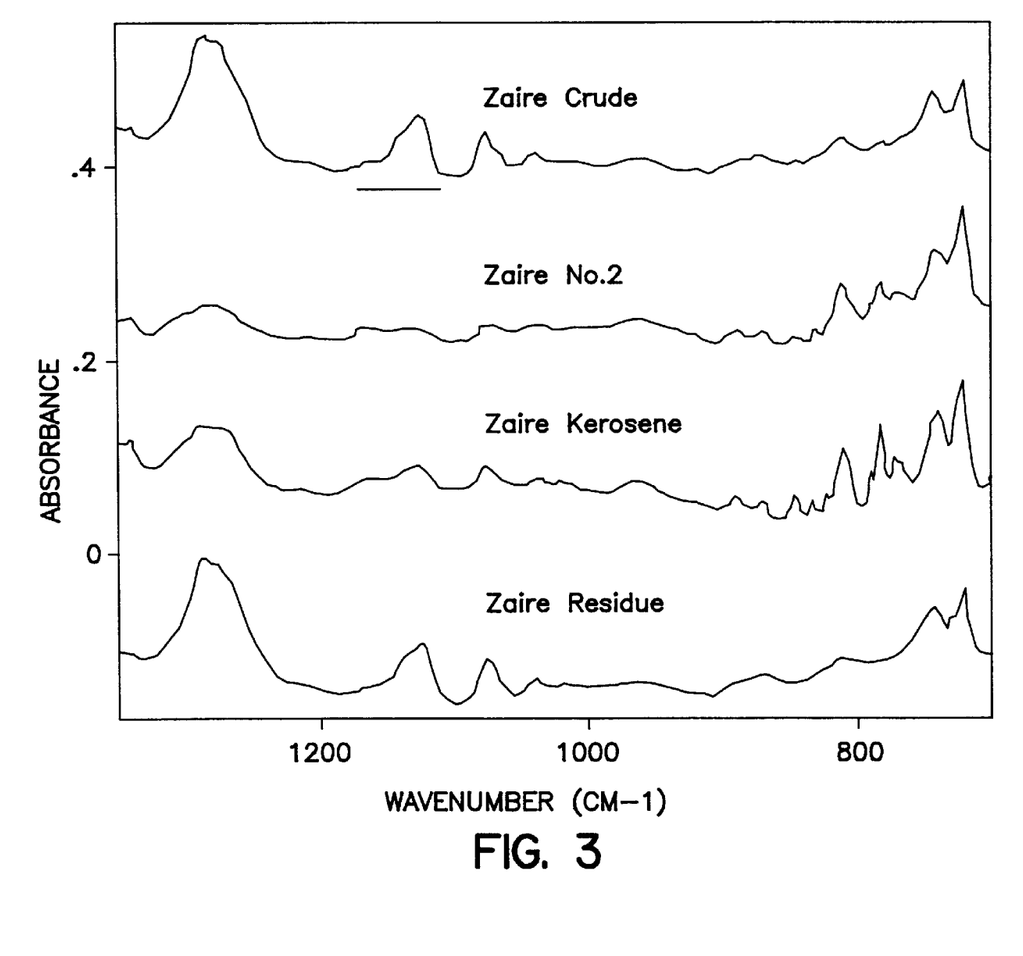
FIG. 3 is a graph of the evanescent wave of a Zaire crude, its distillates and its residual.

Evanescent wave spectra of thirty samples of crude oils and their distillate products have been measured. Absorbance spectra in the region of 1350–700 cm$^{-1}$ of a crude oil from Zaire and its kerosene, No. 2 fuel and residual are shown in FIG. 3. There are many sharp bands in the region of 900–700 cm$^{-1}$. These bands are characteristic of petroleum samples, and provide a unique fingerprint of each individual sample. As we can see from the spectra, the kerosene and the No. 2 fuel have more and sharper bands than the crude oil they come from. The kerosene and the No. 2 fuel have similar bands in this region, but the relative intensities of these bands are considerably different. The residual has fewer, broader bands than its parent crude oil and the other two distillates.

Figure 4:
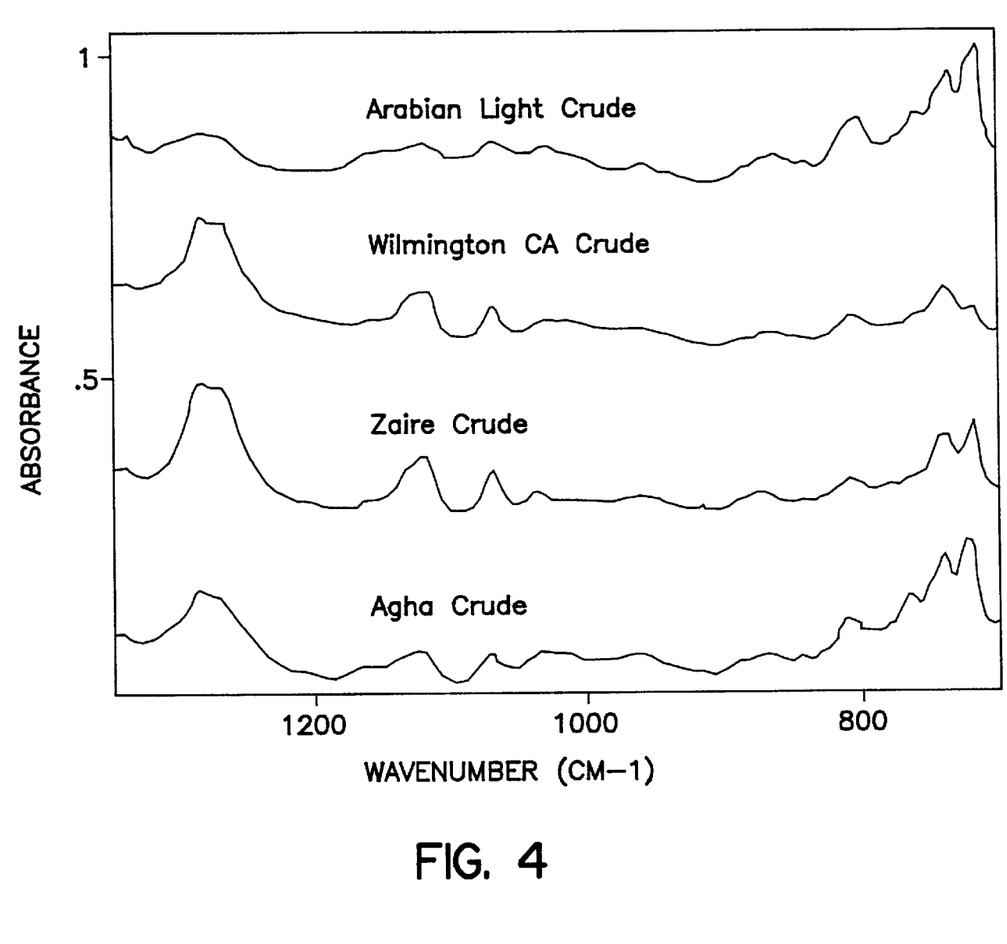
FIG. 4 is a graph of evanescent waves of various crude oils.

Evanescent wave spectra of crude oils from four different sources are shown in FIG. 4. Three samples are from North Africa and the Middle East, whereas the fourth sample is from California. The spectra of crude oils from North Africa/Middle East have similar contours in the region of 900–700 cm$^{-1}$; however, they can be distinguished by the relative intensity differences. The samples from California is different than the other three samples.

Principal Component Analysis of Petroleum Spectra

Classification of sets of similar spectra data is one of the major applications of PCA in spectroscopic analysis, Brown, C. W., *Spectroscopic Multicomponent Analysis*, in press; Beebe, K. R. and Kowalski, B. R., *Anal. Chem.*, 1987, 59, 1007A; and Wold, S., *Chromometr. Intelli. Lab. Sys.*, 1987, 2, 37. In this case, the data set includes absorbance spectra of each samples in rows of the A-matrix. PCA describes this matrix as a product of two matrices as shown in the following equation $$A = UV^t$$

where the V$^t$-matrix contains loading vectors in rows and the U-matrix contains scores. The loading vectors in the V$^t$-matrix are new representations of the original data set; therefore, each of the original spectra in the A-matrix can be described as a linear combination of these new representations. The values in the U or score matrix are the coefficients used in the linear combination of these new representations to reproduce the original spectra. The eigenvalue for each loading vector is the sum of the square scores for that vector. The loading vectors corresponding to the largest eigenvalues contain the most useful information for regenerating the original spectra. The first loading vector represents the most similarity. The differences between the originals spectra are found in the second, third and higher loading vectors. PCA can be used to classify different objects in the data set by using a score plot, which is a plot of scores for one loading vector vs scores for another loading vector.

Figure 5:
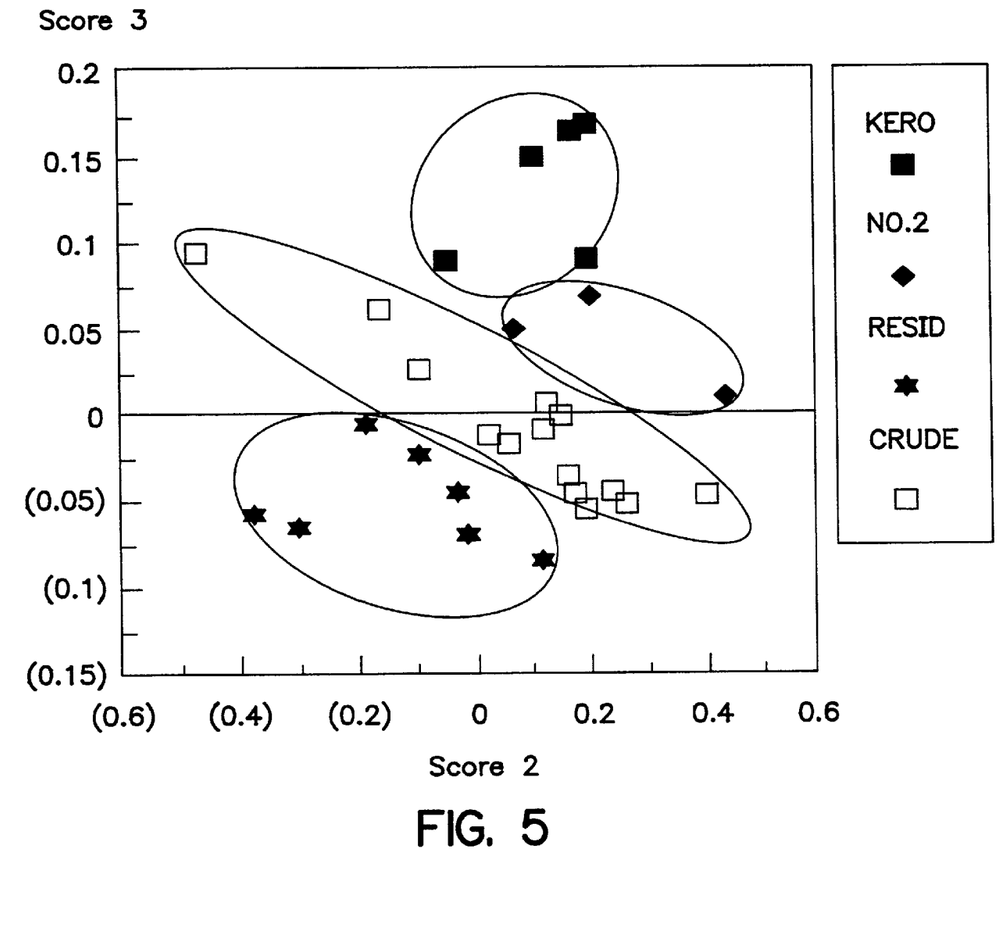
FIG. 5 is a graphic illustration of PCA score plots from the infrared spectra of various petroleum samples.

The thirty petroleum samples including fourteen crude oils, five kerosenes, four No. 2 fuels and seven residuals have been classified using a PCA score plot. The scores for vector 3 vs the scores for vector 2 calculated for the spectral region 1000–700 cm$^{-1}$ are plotted in FIG. 5. Each of the four oil types are clustered together with the crude oils spanning the middle of the plot. The selection of crude oils included both light and heavy crudes, thus, explaining the reason these oils form a much broader cluster that diagonally transverses the plot. The two lighter fractions, kerosenes and NO. 2's appear on the upper right, whereas the heavy residuals appear on the lower left. The scores for the second and third vectors formed the most distinctive sets of clusters; other score plots produced greater overlap among the clusters.

Library Search

Figure 6:
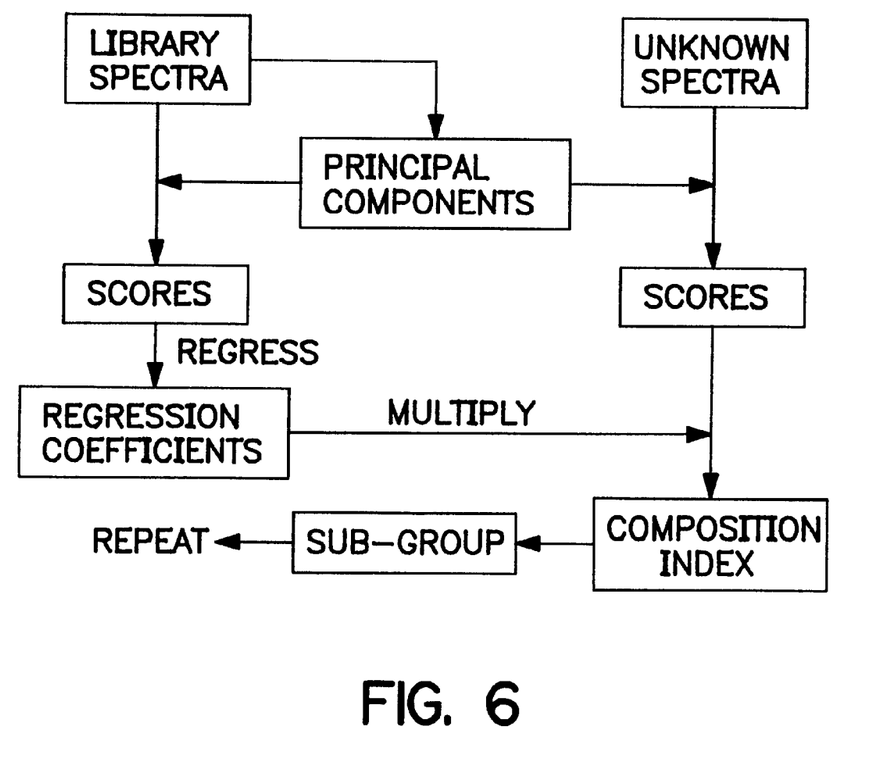
FIG. 6 is a block flow chart for a spectral library search algorithm based on principal component analysis.

In addition to classifying petroleum types from their infrared spectra, we have used spectra of samples from simulated spills as unknowns for searching a library of spectra containing the spectra of the virgin oils. The method for searching a spectral library is described completely elsewhere, Lo, S. and Brown, C. W., *Appl. Spectro.*, 1991, 45, 1621; and Lo, S. and Brown, C. W. , *Appl. Spectro.*, 1991, 45, 1628. A flow chart for establishing a library and searching unknowns is shown in FIG. 6. PCA is applied to the library spectra to find the principal component loading vectors. The scores of the library spectra were calculated from the principal component loading vectors and the concentrations of each library sample (assumed to be 1.0 for each sample) are regressed onto the scores to produce regression coefficients. The unknown spectrum (shown on the right side of the flow chart) is projected onto the principal component loading vectors obtains from the library; the resulting scores are multiplied by the regression coefficients to obtain composition indices, which are pseudo concentrations. A sub group with the top composition indices is used as a new library to develop a second library search. Thirty petroleum samples were used for the first pass, twenty-five loading vectors were selected for the unknown search; ten samples having the top composition indices were selected for the sub group and ten loading vectors were used for the unknown search.

Figure 7:
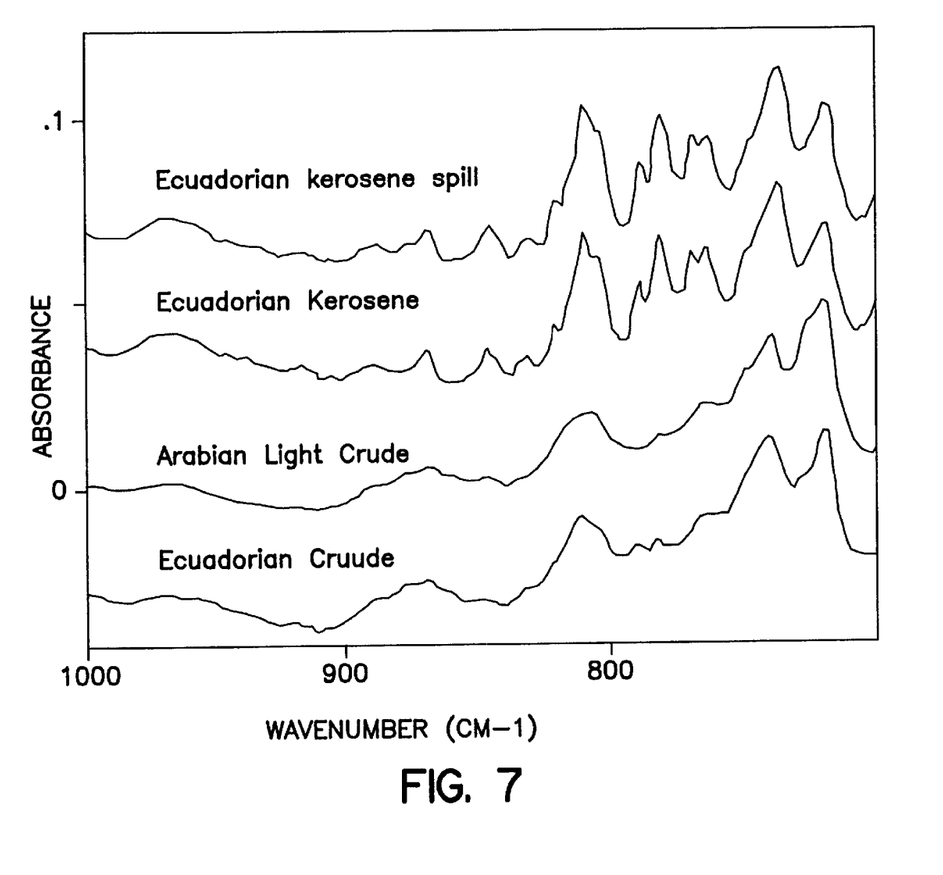
FIG. 7 is a graph of evanescent wave spectra of an Ecuadorian kerosene spill and the closest matching spectra.
Figure 8:
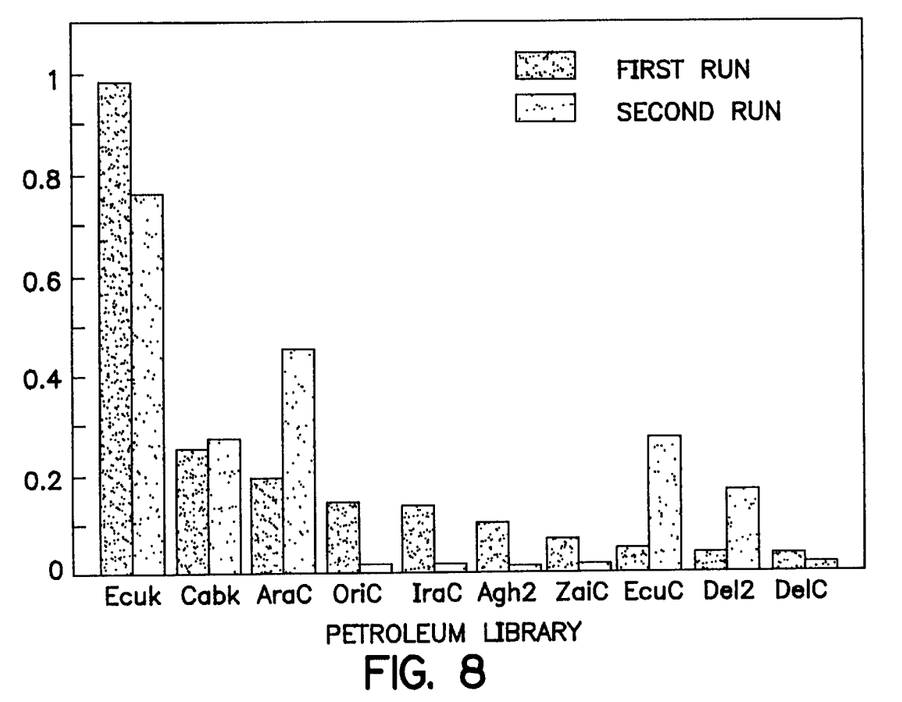
FIG. 8 is a composition indices of ten candidates from searching with the spectrum of an Ecuadorian kerosene spill sample.

The Mix-Match search algorithm was applied to the spectrum of an Ecuadorian kerosene spill (unknown) in the region of 1000–700 cm$^{-1}$. The spectra of the unknown and top three possible samples are shown in FIG. 7. The unknown spectrum is identical to the original spectrum of the Ecuadorian kerosene. During the first pass of the library, the search algorithm selected the Ecuadorian kerosene as the first choice. Ten top candidates with top composition indices were selected for the sub group and the Ecuadorian kerosene was still the first choice; thus, it was confirmed that the oil spill was due to the Ecuadorian kerosene. The compositional indices of the top ten candidates of the library search are displayed in FIG. 8.

Spills of five crude oils, one No. 2 fuel, one kerosene and one residual were investigated in this search. Six of the unknowns were correctly identified during the first pass through the library; two samples, Zaire No. 2 and Arabian crude, were correctly identified during the second pass. Thus, the methods selected the correct source in all eight cases. Generally, the second pass confirmed the results of the first pass. For cases in which there were several similar spectra in the library, the second pass was required for positive identification.

The method of the invention provides rapid and remote detection of petroleum, the capability to classify petroleum samples, and the capability to identify unknown petroleum samples from spills. The silver halide fiber can be placed in the petroleum samples directly to measure evanescent wave spectra of the petroleum. Thus, the entire system is very easy to use for the remote detection and monitoring.

The evanescent wave spectra of petroleum samples in the mid-infrared region coupled with principal component analysis have been used to classify crude oils, No. 2 fuels, kerosenes and the residual distillates. All four petroleum types form distinctive clusters which can be used for classification.

A library search of petroleum samples from simulated spills has also been tested using a recently developed pattern recognition algorithm. This is a rapid, accurate technique for identifying the source of oil spills. It takes less than one minute to perform the search. With the system and method of the invention, eight out of eight samples were correctly identified.

Figure 9:
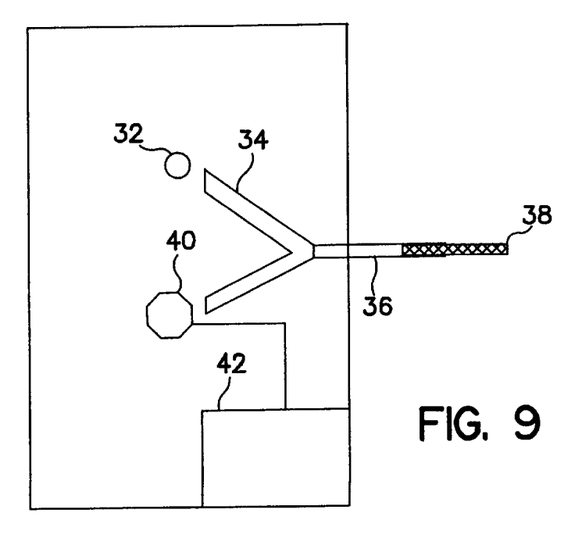
FIG. 9 is a schematic of a portable sensor embodying the invention.

Referring to FIG. 9, a portable sensor is shown and comprises an infrared light source 32 in optical communication with a hollow waveguide 34 for transmitting the light into a fiber optic element 36. At the distal end of the optic fiber 36 is a gold mirror 38 to reflect the light in the fiber optic 36. The wave guide 34 transmits the reflected light to an array detector 40. The array detector may comprise two to ten detecting elements for wavelength specific to oil. The detector electronics is shown generally at 42. The electronics 42 can transmit any signals to remote locations as desired.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A fiber optic sensor for the detection of hydrocarbons which comprises:

a metal halide fiber optic having a refractive index greater than the refractive index of the hydrocarbons to be detected, the fiber optic characterized by a non-cladded portion;

means to place the non-cladded portion in a sample containing hydrocarbons;

means to transmit a signal through the fiber optic to and from the sample; and means to obtain an evanescent spectrum of the hydrocarbon sample from the non-cladded portion.

2. The fiber optic sensor of claim 1, wherein the evanescent spectrum is a fingerprint of the sample and which comprises:

means to compare the evanescent spectrum of the hydrocarbon sample to a library of evanescent spectra to determine the identity of the evanescent spectrum.

3. The fiber optic sensor of claim 1, wherein the fiber optic is a silver halide.

4. The fiber optic sensor of claim 1, wherein the halide is selected from the group consisting of chloride or bromide.

5. The fiber optic sensor of claim 1 wherein the fiber optic has a refractive index of 2.2.

* * * * *